US011000239B2

(12) United States Patent
Miller et al.

(10) Patent No.: US 11,000,239 B2
(45) Date of Patent: *May 11, 2021

(54) METHODS, SYSTEMS, AND APPARATUS FOR DETERMINING RADIATION DOSES

(71) Applicant: General Electric Company, Schenectady, NY (US)

(72) Inventors: David E. Miller, Kirkland, WA (US); Pierre Guntzer, Strasbourg (FR)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,785

(22) Filed: May 27, 2020

(65) Prior Publication Data

US 2020/0281544 A1 Sep. 10, 2020

Related U.S. Application Data

(63) Continuation of application No. 15/706,279, filed on Sep. 15, 2017, now Pat. No. 10,702,219.

(51) Int. Cl.
| | | |
|---|---|---|
| *A61B 6/03* | (2006.01) | |
| *A61B 6/00* | (2006.01) | |
| *G09B 23/28* | (2006.01) | |
| *G06K 9/00* | (2006.01) | |
| *G06T 7/00* | (2017.01) | |

(52) U.S. Cl.
CPC .............. *A61B 6/032* (2013.01); *A61B 6/488* (2013.01); *A61B 6/5294* (2013.01); *A61B 6/542* (2013.01);

(Continued)

(58) Field of Classification Search
CPC ......... A61B 6/032; A61B 6/545; A61B 6/544; A61B 6/56; A61B 6/488; A61B 6/5294;
(Continued)

(56) References Cited

U.S. PATENT DOCUMENTS 9,649,079 B1 * 5/2017 Guntzer ............... G09B 23/286
10,463,317 B2 11/2019 Tian et al.
(Continued)

FOREIGN PATENT DOCUMENTS

KR 10-2017-0060698 6/2017

OTHER PUBLICATIONS

Imaging Technology News, "GE Healthcare to License Duke University's CT Organ Dosimetry Technology", Jul. 31, 2017, 1 page.
(Continued)

*Primary Examiner* — Michael C Bryant
(74) *Attorney, Agent, or Firm* — Hanley, Flight & Zimmerman, LLC

(57) ABSTRACT

Methods and apparatus for determining radiation doses based on phantom matching are disclosed. An example apparatus includes an image processor to process a scout image to determine the first dimensions of an anatomical landmark of the scout image file; a comparator to select a phantom model based on the first dimensions, the phantom model including the anatomical landmark with second dimensions substantially similar to the first dimensions; and a dose calculator to calculate a radiation dose for an organ in the anatomical landmark based on the selected phantom.

20 Claims, 8 Drawing Sheets

(52) U.S. Cl.
CPC .............. *A61B 6/544* (2013.01); *A61B 6/545* (2013.01); *A61B 6/56* (2013.01); *A61B 6/566* (2013.01); *G06K 9/00362* (2013.01); *G09B 23/28* (2013.01); *A61B 6/465* (2013.01); *A61B 6/467* (2013.01); *G06T 7/0012* (2013.01)

(58) Field of Classification Search
CPC ......... A61B 6/566; A61B 6/542; A61B 6/465; A61B 6/467; G06T 7/0012; G06K 9/00362

See application file for complete search history.

(56) References Cited

U.S. PATENT DOCUMENTS

| | | | | |
|---|---|---|---|---|
| 2012/0148132 | A1* | 6/2012 | Couch | G16H 50/50 382/131 |
| 2014/0078139 | A1* | 3/2014 | Park | A61B 17/122 345/420 |
| 2016/0166224 | A1 | 6/2016 | Zhou | |
| 2017/0143291 | A1 | 5/2017 | Guntzer et al. | |
| 2017/0224302 | A1 | 8/2017 | Von Berg et al. | |
| 2019/0083047 | A1 | 3/2019 | Miller et al. | |

OTHER PUBLICATIONS

United States Patent and Trademark Office, "Non-Final Office Action", issued in connection with U.S. Appl. No. 15/706,279 dated Nov. 4, 2019, 7 pages.

United States Patent and Trademark Office, "Notice of Allowance and Fee(s) Due", issued in connection with U.S. Appl. No. 15/706,279 dated Feb. 26, 2020, 9 pages.

International Searching Authority, "International Search Report and Written Opinion", issued in connection with application No. PCT/US2018/043279 dated Nov. 7, 2018, 11 pages.

* cited by examiner

METHODS, SYSTEMS, AND APPARATUS FOR DETERMINING RADIATION DOSES

FIELD OF THE DISCLOSURE

This patent arises from a continuation of U.S. patent application Ser. No. 15/706,279, (Now U.S. Pat. No. 10,702, 219) which was filed on Sep. 15, 2017. U.S. patent application Ser. No. 15/706,279 is hereby incorporated herein by reference in its entirety. Priority to U.S. patent application Ser. No. 15/706,279 is hereby claimed.

FIELD OF THE DISCLOSURE

This disclosure relates generally to ionizing radiation (e.g., x-rays), and, more particularly, to methods, systems, and apparatus for determining radiation doses based on phantom matching.

BACKGROUND

In non-invasive imaging systems, x-ray tubes are used in various x-ray systems and computed tomography (CT) systems as a source of ionizing (x-ray) radiation. The ionizing radiation is emitted in response to control signals during an examination or imaging sequence. An emitter within the cathode emits a stream of electrons in response to heat resulting from an applied electrical current, and/or an electric field resulting from an applied voltage to a properly shaped metallic plate in front of the emitter. The anode includes a target that is impacted by the stream of electrons. The target, as a result of impact by the electron beam, produces x-ray radiation to be emitted toward an imaged volume. In such imaging systems, a portion of the radiation passes through a subject of interest, such as a patient, baggage, or an article of manufacture, and impacts a digital detector or a photographic plate where the image data is collected. The signals are then processed to generate an image that may be displayed for review. In other systems, such as systems for oncological radiation treatment, a source of x-rays is used to direct ionizing radiation toward a target tissue. Regardless of the type of x-ray system used, it is beneficial to know the amount (dose) of x-ray exposure during individual imaging or treatment events.

Accordingly, one concern with ionizing radiation includes an increased likelihood of harm or injury associated with radiation-induced injury to the tissue of the exposed subject. A variable that affects a likelihood of causing radiation-induced injury to tissue of an exposed subject is the dose or amount of radiation absorbed by the exposed subject. Variables that affect a dose of radiation absorbed by the exposed subject include a rate of delivery of radiation, a time of exposure of radiation, a fraction of radiation absorbed by the exposed subject, age, or other characteristics of the exposed subject, and location of radiation exposure on the exposed subject. Another concern with use of ionizing radiation includes an increased likelihood of causing effects (e.g., radiation—induced cancers) to the exposed subject.

BRIEF SUMMARY

Certain examples provide an apparatus for determining radiation dose based on phantom matching. The example apparatus includes an image processor configured to process a scout image to determine a first set of dimensions of an anatomical landmark of the scout image file. The example apparatus further includes a comparator configured to select a phantom model based on the first set of dimensions, the phantom model including the anatomical landmark with a second set of dimensions that match the first set of dimensions. The example apparatus further includes a dose calculator configured to calculate a radiation dose for an organ in the anatomical landmark based on the selected phantom.

Certain examples provide a method for determining radiation dose based on phantom matching. The example method includes processing, by executing an instruction using a processor, a scout image to determine a first set of dimensions of an anatomical landmark of the scout image file. The example method further includes selecting, by executing an instruction using the processor, a phantom model based on the first set of dimensions, the phantom model including the anatomical landmark with a second set of dimensions that match the first set of dimensions. The example method further includes calculating, by executing an instruction using the processor, a radiation dose for an organ in the anatomical landmark based on the selected phantom.

Certain examples provide a computer readable storage medium comprising instructions which, when executed, cause a machine to determine radiation dose based on phantom matching. The example computer readable medium includes instructions to cause a machine to process a scout image to determine a first set of first dimensions of an anatomical landmark of the scout image file. The example instructions further cause the machine to select a phantom model based on the first set of dimensions, the phantom model including the anatomical landmark with a second set of dimensions that match the first set of dimensions. The example instructions further cause the machine to calculate a radiation dose for an organ in the anatomical landmark based on the selected phantom.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
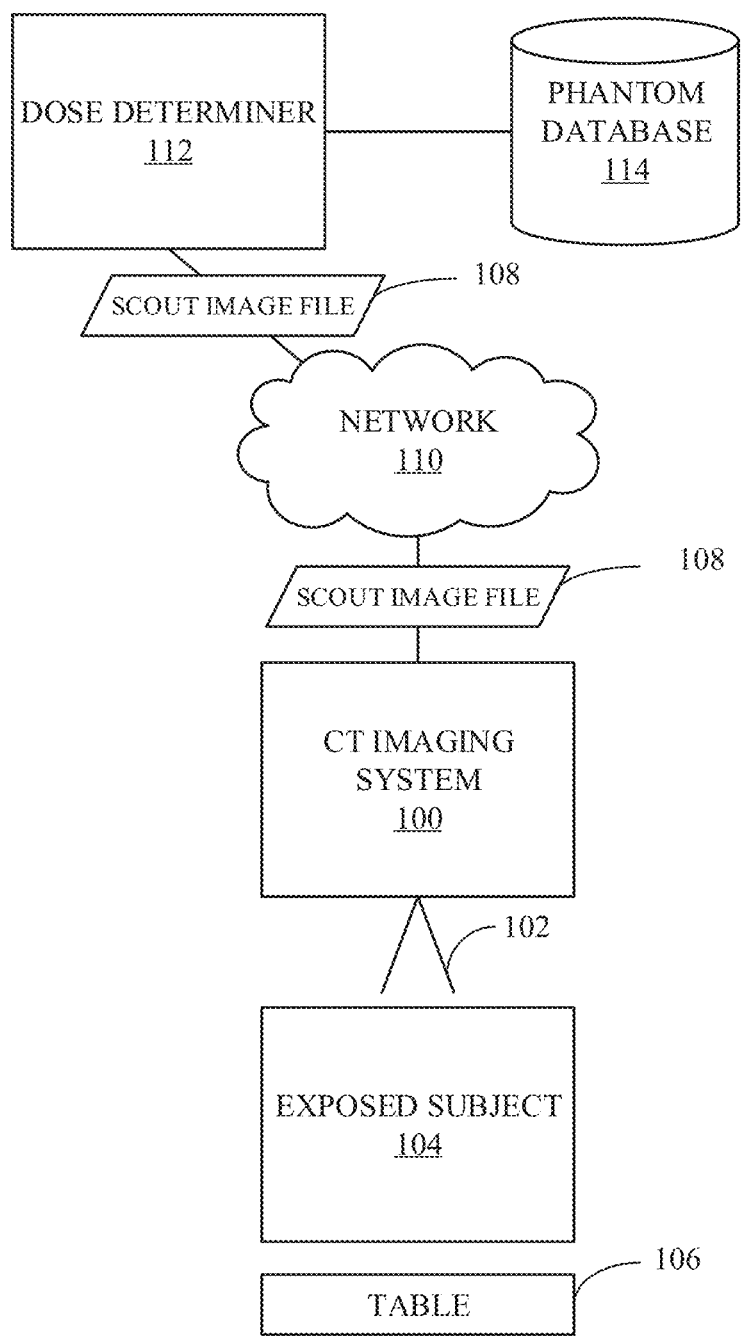
FIG. 1 is an illustration of an example environment for determining radiation doses based on phantom matching.

For computed tomography (CT), one example metric/method to estimate irradiation dose normalized with patient anatomy is water equivalent diameter. This method includes determining the diameter of a cylinder of water which has the same x-ray attenuation as the patient in the irradiated region. An aim of the method is to normalize the standard CT dose index volume ($CTDI_{vol}$) dose metric according to the nature of the tissues crossed.

A Digital Imaging and Communications in Medicine (DICOM) image file generally includes a collection or series of tags where each tag includes pixel data having a value that represents the pixel associated with the tag. The remaining tags of a DICOM image file, other than the pixel data tags, are referred to as metadata. The pixel data tags of the DICOM image can represent a DICOM scout or localizer image (also referred to as a "scout image" or "localizer"). A scout or localizer image can be sent by a device in combination with a series of image slices, for example. In certain examples, the scout image is a two-dimensional DICOM image of an orientation (e.g., defined by X and Y axes) having been acquired along an X-axis of the CT device, which corresponds to a horizontal axis extending in a direction from a left-hand border to a right-hand border of a surface of the table, and a Y-axis which corresponds to a vertical axis extending in a direction from the floor upward in direction toward a top of the table. One example of an acquired image file includes a series of images containing the scout image as well as other images.

In the field of CT scanning, conventionally, the weight, age, and/or gender of a patient are determined prior to the scan to calculate the dose of radiation to be administered to the patient. The dose of radiation is determined based on the measured weight, age, and/or gender. However, weight, age, and/or gender may not accurately correspond with an appropriate receiving dose of radiation. With the usage rates of CT scans on the rise, minimizing the dose of radiation a patient receives is beneficial.

According to the present disclosure, one method of determining the receiving dose for a patient prior to scanning includes performing an initial topographic scan (e.g., a scout image) on the patient. This scout image gives a rudimentary image of the patient that may be compared to voxelized phantom models (e.g., models of phantoms digitized at a voxel level) stored in a database. A phantom model that matches the scout image is then identified and a dose is determined for the patient based on the dose corresponding to the matched phantom model. Conventional techniques include categorizing phantoms based on gender, age, and/or weight. As discussed above, conventional techniques match the patient to a phantom model based on gender, age, and/or weight of the patient. However, the match based on gender, age, and/or weight and weight may not be accurate for people of the same body weight, gender, and/or age but different dimensions, thereby leading to inaccurate doses. For example, the dimensions (e.g., a set of measurements of a set of dimensions) of the patient may include a large chest and a small abdomen while the phantom model may include a small chest and a large abdomen, thereby corresponding to different appropriate radiation doses. Accordingly, examples disclosed herein match the scout image of the patient to the phantom model based on dimensions of anatomical landmark(s) (e.g., head, chest, abdomen, etc.). In particular, examples include processing scout images to identify anatomical landmark(s) and determining (A) what anatomical landmark(s) are included in the scout image and (B) the dimensions of the determined anatomical landmark(s). Examples disclosed herein further include matching the scout image with at least one of the phantom models based on the dimensions of the anatomical landmark(s) as opposed to matching based on weight, age, and/or gender. Examples disclosed herein increase the accuracy of radiation dose administered to the patient, helping to ensure that high quality CT images are acquired at the least possible dose of radiation.

FIG. 1 illustrates an example environment for determining radiation doses based on phantom matching. As illustrated in FIG. 1, in some embodiments, the environment includes a CT imaging system 100, an ionizing radiation 102, an exposed subject 104, a table 106, a scout image file 108, a network 110, a dose determiner 112, and a phantom database 114. A radiation dose can be tracked and reported during or in an image acquisition procedure or other protocol involving direction of ionizing radiation 102 toward the exposed subject 104 supported on the table 106. Although the dose determiner 112 can be located remote from the CT imaging system 100 of FIG. 1, the dose determiner 112 can otherwise be integrated with or located adjacent to the CT imaging system 100 of FIG. 1.

The CT imaging system 100 of FIG. 1 can be an angiographic imaging system, CT, a fluoroscopic imaging system, etc., having a radiation source projecting the beam of ionizing radiation (e.g., x-rays) 102 toward the exposed subject 104. The ionizing radiation 102 can be attenuated with passing through exposed subject 104 and then received at a detector, which translates the attenuation of ionizing radiation to generate DICOM anterior/posterior (AP) scout image data files in electronic format (e.g., the scout image file 108). The scout image can display or illustrate a region of interest of the exposed subject 104. The CT imaging system 100 generates the DICOM AP scout image or image file (herein "scout image file") 108, as well as stores a scanning range associated with the DICOM AP scout image file 108, for communication to the dose determiner 112 (e.g., via the network 110).

In some embodiments, the scout image file 108 includes a collection or series of tags (similar in concept to .xml or .html tags) where each tag includes pixel data having a value that represents the pixel (e.g., basic unit of programmable color on a display monitor) associated with the tag. The remaining tags of a scout image file 108, other than the pixel data tags, can be referred to as metadata. The pixel data tags of the scout image file 108 can include a DICOM scout or localizer image or image file (herein "scout image") in combination with a series of image slices. The scout image can be a two-dimensional DICOM instance or image of an orientation (e.g., defined by X and Y axes). The scout image is obtained along (A) an X-axis (e.g., corresponding to a horizontal axis) extending in a direction from a left-hand border to a right-hand border of a surface of the table 106 and (B) a Y-axis (e.g., corresponding to an axis perpendicular to the X-axis in the horizontal plane) extending from the lower limbs of the exposed subject 104 to his head. One example of an acquired image file includes a series that includes the scout image and the remaining images may be the "slices" or slice images (not shown) of patient image data.

One example of the scout image is a front planar view (e.g. a projection image of the exposed subject 104 resting on the table 106) of the relevant portion of interest of the exposed subject 104, while the slice images are cross-sectional diagnostic images of the exposed subject 104. The scout image can be a general illustration of the projected view of the exposed subject 104 different with respect to the slice images. The scout image can be generated to show a location of each of the acquired slice images relative to other acquired slices and their location with respect to the exposed subject 104. An illustration of the location of each of the slice images with respect to the scout image can be indicated by, for example, a graphic line created for display in the scout image. From graphic illustration of the scout image, a user can select with a pointer, mouse or similar input selector device the particular graphic line associated with one of the series of slice images for detailed viewing. The illustration of the graphic line in the scout image can change positions to reflect a position of the slice of current interest for detailed viewing. The scout image generally has lower image resolution relative to the series of image slices.

The network 110 can facilitate transmission of electronic or digital data within and/or among the environment of FIG. 1. The network 110 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN), a local area network (LAN), the Internet, a cloud-based computing infrastructure of computers, routers, servers, gateways, etc., or any combination thereof that allows the dose determiner 112 to communicate with the CT imaging system 100. With respect to the example implementation of the network 110 including a cloud-based infrastructure, components in the environment of FIG. 1 can share information via web-based applications, cloud storage and cloud services. For example, a Web-based portal may be used to facilitate access to information, etc. The Web-based portal can be a central interface to access information and applications, and data may be viewed through the Web-based portal or viewer, for example. Additionally, data may be manipulated and propagated using the Web-based portal, for example. The Web-based portal can be accessible locally (e.g., in an office, in an operating room, in a radiology reading room, etc.) and/or remotely (e.g., via the Internet and/or other network or connection), for example.

The dose determiner 112 receives the scout image file 108 from the CT imaging system 100 (e.g., via the network 110) and determines a local dose of radiation for an anatomical stage or region based on a comparison of the scout image file 108 to a voxelized phantom model (e.g., hereinafter "phantom") stored in the phantom database 114. The phantom database 114 includes phantoms for various body types. A phantom is a specially designed object that is scanned or imaged to evaluate, analyze, and/or tune performance of various imaging devices. Phantoms used to evaluate an imaging device respond in a similar manner to how human tissues and/or organs would act in that specific imaging modality. Accordingly, the characteristics of a phantom that matches a scout image can be used for an accurate determination of dose for a patient for whom the scout image file 108 is generated. As described above, matching the scout image file 108 to a phantom with similar dimensions provides a better local dose than determining the local dose based on the weight, age, and/or gender of a patient. Although the illustrated example shows that the phantom database 114 is connected to the dose determiner 112, the phantom database 114 may be located within the dose determiner 112 or may be implemented as a stand-alone device connected directly and/or indirectly (e.g., via the network 110) to the dose determiner 112.

In some examples, once the dose determiner 112 receives the scout image file 108, the dose determiner 112 pre-processes the scout image file 108. For example, the dose determiner 112 can apply convolution filters (e.g., median filters, Gaussian blur filters, etc.) to the scout image file 108. Pre-processing the scout image file 108 aids in calculating the contour of an extremity (e.g., the exterior or skin surface) of the exposed subject 104 and/or the anatomic landmarks of the exposed subject 104 from the scout image file 108. In some examples, the dose determiner 112 calculates the contour of the extremity by image processing such as comparing or analyzing a greyscale intensity of the candidate pixels comprising the scout image file 108 to define the contour. Image processing can further include analysis or comparison of a geometric location of the candidate pixels relative to a predefined reference. Based on the analysis, the dose determiner 112 determines a score for each of the candidate pixels to define the contour of the extremity. Dependent on a comparison of the scores of the candidate pixels to one another, the dose determiner 112 can identify and enhance display of the subset of candidate pixels (e.g., create overlying a new line, increase width of candidate pixels, increase greyscale intensity, or combination thereof, etc.) to further differentiate the illustration of the contour of the extremity from other pixels that are included in the acquired scout image file 108.

The dose determiner 112 determines anatomic landmarks (e.g., head, shoulders, chest, abdomen, pelvis, etc.) of the scout image file 108 by delineating the contour of the scout image file 108. The delineation may include image processing directed to identify pixels of greyscale intensity and width associated with a high increase in exposed subject thickness. Methods for determining anatomic landmarks are described in U.S. patent application Ser. No. 14/510,815 (issued as U.S. Pat. No. 9,649,079), which is herein incorporated in its entirety by reference.

The dose determiner 112 determines the dimensions of the anatomic landmarks in the scout image file 108 based on the delineation. In some examples, the dose determiner 112 determines the dimensions of an anatomic landmark based on the upper limit of the anatomic landmark and the lower limit of the anatomic landmark, where the dimensions correspond to the distance between the top of an anatomic landmark (e.g., the top of a chest/bottom of shoulders) and the bottom of an anatomic landmark (e.g., bottom of the chest/top of the abdomen) in the longitudinal direction. In some examples, the dimensions may additionally or alternatively include the contour of the scout image file (e.g., the distance between each side of the anatomic landmark in a latitudinal direction). Once the dimensions of the anatomic landmarks are determined, the dose determiner 112 selects a phantom from the phantom database 114 that matches the dimension(s) of anatomic landmarks of interest. For example, if the local dose corresponds to a radiation within the chest region, the dose determiner 112 selects a phantom whose chest dimensions match the determined chest dimensions of the scout image file 108. In some examples, the matching may be based on a difference between the dimensions of an anatomic landmark of a phantom and the dimensions of the anatomic landmark of the scout image file 108 being less than a predefined threshold. In some examples, the matching is based on the anatomic landmark of the phantom whose dimensions most closely align with the dimensions of the anatomic landmark of the scout image file 108 (e.g., the difference between the phantom dimensions and the scout image dimensions are smaller than the difference of any other phantom in the example phantom storage 114 of FIG. 1). In another example, if the local dose corresponds to radiation within the chest and abdomen region, the dose determiner 112 selects a phantom whose chest and abdomen dimensions match the determined chest and abdomen dimensions of the scout image file 108. In some examples, the dose determiner 112 selects the phantom based on the below equation:

$$\text{Score}=\Sigma_{i\in(regions\ detected)}|h_i(\text{phantom})-h_i(\text{patient})| \quad \text{(Equation 1)}$$

Equation 1 represents the sum of the difference between the heights of the patient and a phantom for each region detected, thereby resulting in a score. The comparison with the lowest score corresponds to the best match between the scout image of the patient and the phantom.

The dose determiner 112 of FIG. 1 calculates the local dose based on the below equation:

$$H = \frac{\sum_{z \in (organ)} D_{ratio,z} \times N_z}{\sum_{z \in (organ)} N_z} \times CTDI_{vol} \times h_{organ} \quad \text{(Equation 2)}$$

Where H is the total dose for a particular organ, z is the location of the organ, $N_z$ is the number of organ pixels at location z of the selected phantom(s), $CTDI_{vol}$ is a volume CT dose index corresponding to the actual radiation (e.g., the ionizing radiation 102), and $h_{organ}$ corresponds to the size of the exposed subject 104 and correction factors based on the size of the exposed subject 104. In some embodiments, $h_{organ} = e^{(\alpha d + \beta)}$, where d corresponds to the size of the exposed subject 104 based on the determined contour and $\alpha$ and $\beta$ are correction factors corresponding to the size of the exposed subject 104. $D_{ratio,z}$ is a ratio corresponding to a tube current modulation (TCM) profile ($D_{TCM,CTDI}$) over the fixed tube current ($D_{TCM,CTDI}$)

$$\left( e.g., D_{ratio,z} = \frac{D_{TCM,CTDI}}{D_{fixed,CTDI}} \right).$$

The dose spread ratio may be convolved with the TCM profile and the fixed tube current respectively to derive the accumulated dose distribution.

Figure 2:
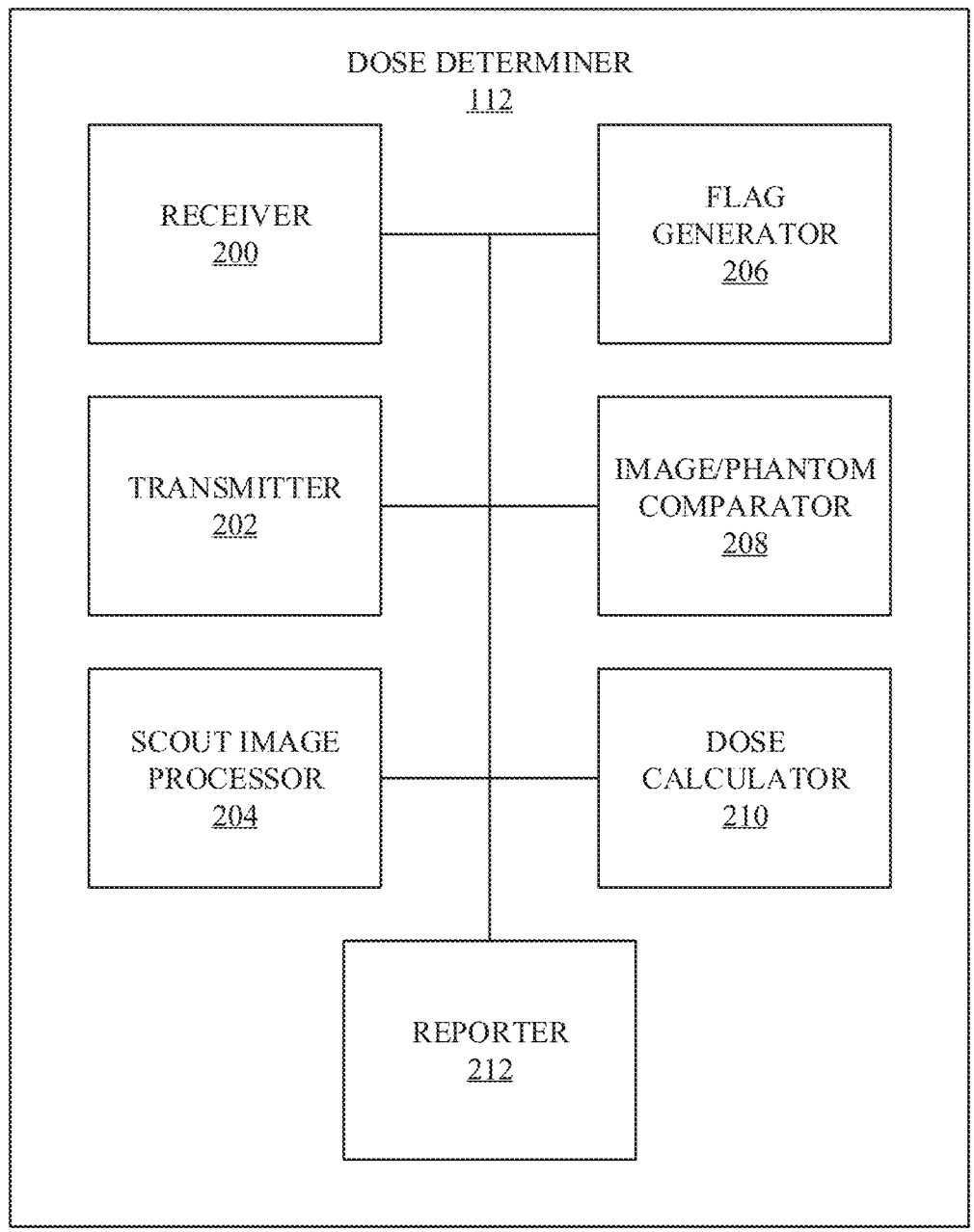
FIG. 2 is a block diagram of an example dose determiner that can be used in the environment of FIG. 1.

FIG. 2 is a block diagram of an example implementation for the dose determiner 112 of FIG. 1. The dose determiner 112 of the example of FIG. 2 is structured to determine local radiation doses for one or more organs. The dose determiner 112 of FIG. 2 includes a receiver 200, a transmitter 202, a scout image processor 204, a flag generator 206, an image/phantom comparator 208, a dose calculator 210, and a reporter 212.

The receiver 200 receives the scout image file 108 from the CT imaging system 100 (e.g., via the network 110). Additionally, the receiver 200 receives phantoms from the phantom database 114, and/or otherwise allows the dose determiner 112 to interface with the phantom database 114 to select a phantom based on anatomic landmarks of the scout image file 108. The transmitter 202 transmits reports and/or local dose data to the CT imaging system 100 and/or transmits instructions for phantoms from the phantom database 114 that match anatomic landmarks of the scout image file 108.

The scout image processor 204 processes the received scout image file 108. In some examples, the scout image processor 204 pre-processes the scout image file 108 by applying filters to the scout image file 108 (e.g., to make further processing easier), as described above in conjunction with FIG. 1. The scout image processor 204 determines the contour of scout image file 108 to determine the dimensions of the exposed subject 104. The scout image processor 204 can compare or analyze a greyscale intensity of the candidate pixels comprising the scout image file 108 to define the contour. Additionally, the scout image processor 204 determines which anatomic landmarks are within the scout image file 108 and identifies the dimensions of the anatomic landmarks.

The flag generator 206 flags the scout image file 108 when an anatomic landmark cannot be determined based on the scout image file 108. When the scout image file 108 is flagged, the transmitter 202 can transmit the flag to the CT imaging system 100 to prompt a technician to provide another image. Additionally, the CT imaging system 100 may provide details as to why the previous scout image file was flagged. In some examples, the flag generator 206 flags the scout image file 108 when the anatomic landmark dimensions are abnormal. In such examples, a further verification may be needed from a technician to continue to determine a dose. In some examples, if there is not a phantom stored in the phantom database 114 that matches the scout image file 108, the flag generator 206 may flag the scout image file 108. In some examples, the matching may be based on a difference between the dimensions of an anatomic landmark of a phantom and the dimensions of the anatomic landmark of the scout image file 108 being less than a predefined threshold. In some examples, the matching is based on the anatomic landmark of the phantom whose dimensions most closely align with the dimensions of the anatomic landmark of the scout image file 108 (e.g., the difference between the phantom dimensions and the scout image dimensions are smaller than the difference of any other phantom in the example phantom storage 114 of FIG. 1). In some examples, the flag generator 206 flags the scout image file 108 when the scout image does not include the organ whose dose is to be calculated. For example, if the scout image file 108 is tagged to determine a local dose for a heart, and the scout image file 108 does not include a chest (e.g., the anatomic landmark corresponding to the heart), the flag generator 206 flags the scout image file 108.

The image/phantom comparator 208 matches the scout image file 108 with a phantom of the phantom database 114 based on the dimensions of an anatomic landmark of interest. For example, if the anatomic landmark of interest is the abdomen, the image/phantom comparator 208 selects a phantom whose abdomen dimensions (e.g., delineations) match the abdomen dimensions determined in the scout image file 108. In some examples, the image/phantom comparator 208 matches the phantom with the scout image based on the phantom whose anatomic landmark dimensions are closest to the anatomic landmark dimensions of the scout image. For example, the image/phantom comparator 208 determines a difference between the anatomic landmark dimensions of the scout image and the anatomic landmark dimensions of each of the phantoms in the example phantom database 114. In such an example, the image/phantom comparator 208 matches the scout image with the phantom based on the smallest difference. In other examples, the image/phantom comparator 208 matches the phantom with the scout image based on a difference between the anatomic landmark dimensions of the phantom and the anatomic landmark dimensions of the scout image being below a threshold. For example, if the threshold is two centimeters, then the image/phantom comparator 208 may select a phantom based on the difference of the anatomic landmark dimensions of the phantom (e.g., phantom chest length=15 cm) and the anatomic landmark dimensions of the scout image (e.g., scout image chest length=14 cm) being less than two centimeters (e.g., 15 cm−14 cm=1 cm).

In some examples, the image/phantom comparator 208 interfaces with the phantom database 114 to select a matching phantom. In some examples, the image/phantom comparator 208 transmits instructions to the phantom database 114, the instructions including the dimensions of the anatomic landmark of interest and/or an error range (e.g., by how much the phantom dimensions can vary from the scout image file dimensions). In response to receiving the instructions, the phantom database 114 can select a phantom corresponding to the instructions and transmit the phantom data to the dose determiner 112 for further processing.

Once the phantom data corresponding to a matched phantom is received (e.g., by the receiver 200), the dose calculator 210 of FIG. 2 calculates the dose based on the characteristics of the selected phantom. The dose calculator 210 may calculate the dose based on characteristics of the phantom, correction factors based on the contour of the scout image file 108, CTDI volume coefficients, and/or dose spread function coefficients, for example. In some examples, the dose calculator 210 uses the above Equation 2 to determine the appropriate local dose for the exposed subject 104.

The reporter 212 generates a report including the calculated dose corresponding to a desired organ. The report can also include data corresponding to the scout image file 108 and/or the matched phantom. The report can be transmitted (e.g., via the transmitter 202) to the CT imaging system 100 and/or to a technician. Additionally, the reporter 212 may store the report locally for future dose calculations (e.g., to determiner doses based on previously determined dose calculations without having to interface with the phantom database 114, etc.).

While example implementations of the dose determiner 112 of FIG. 1 are illustrated in conjunction with FIGS. 1 and 2, processes and/or devices illustrated in conjunction with FIGS. 1 and 2 may be combined, divided, re-arranged, omitted, eliminated and/or implemented in any other way. Further, the receiver 200, the transmitter 202, the scout image processor 204, the flag generator 206, the image/phantom comparator 208, the dose calculator 210, the reporter 212, and/or, more generally, the dose determiner 112 of FIG. 2 may be implemented by hardware, machine readable instructions, software, firmware and/or any combination of hardware, machine readable instructions, software and/or firmware. Thus, for example, any of the receiver 200, the transmitter 202, the scout image processor 204, the flag generator 206, the image/phantom comparator 208, the dose calculator 210, the reporter 212, and/or, more generally, the dose determiner 112 of FIG. 2 can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the receiver 200, the transmitter 202, the scout image processor 204, the flag generator 206, the image/phantom comparator 208, the dose calculator 210, the reporter 212, and/or, more generally, the dose determiner 112 of FIG. 2 is/are hereby expressly defined to include a tangible computer readable storage device or storage disk such as a memory, a digital versatile disk (DVD), a compact disk (CD), a Blu-ray disk, etc. storing the software and/or firmware. Further still, the dose determiner 112 of FIG. 2 include elements, processes and/or devices in addition to, or instead of, those illustrated in conjunction with FIG. 2, and/or may include more than one of any or all of the illustrated elements, processes and devices.

Flowcharts representative of example machine readable instructions for implementing the dose determiner 112 of FIGS. 1 and/or 2 are shown in conjunction with FIGS. 3-6. Further, although the example program is described with reference to the flowcharts illustrated in conjunction with FIGS. 3-6, many other methods of implementing the dose determiner 112 of FIGS. 1 and/or 2 may alternatively be used. For example, the order of execution of the blocks may be changed, and/or some of the blocks described may be changed, eliminated, or combined. Although the flowcharts of FIGS. 3-6 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of FIGS. 3-6 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 3-6 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 3:
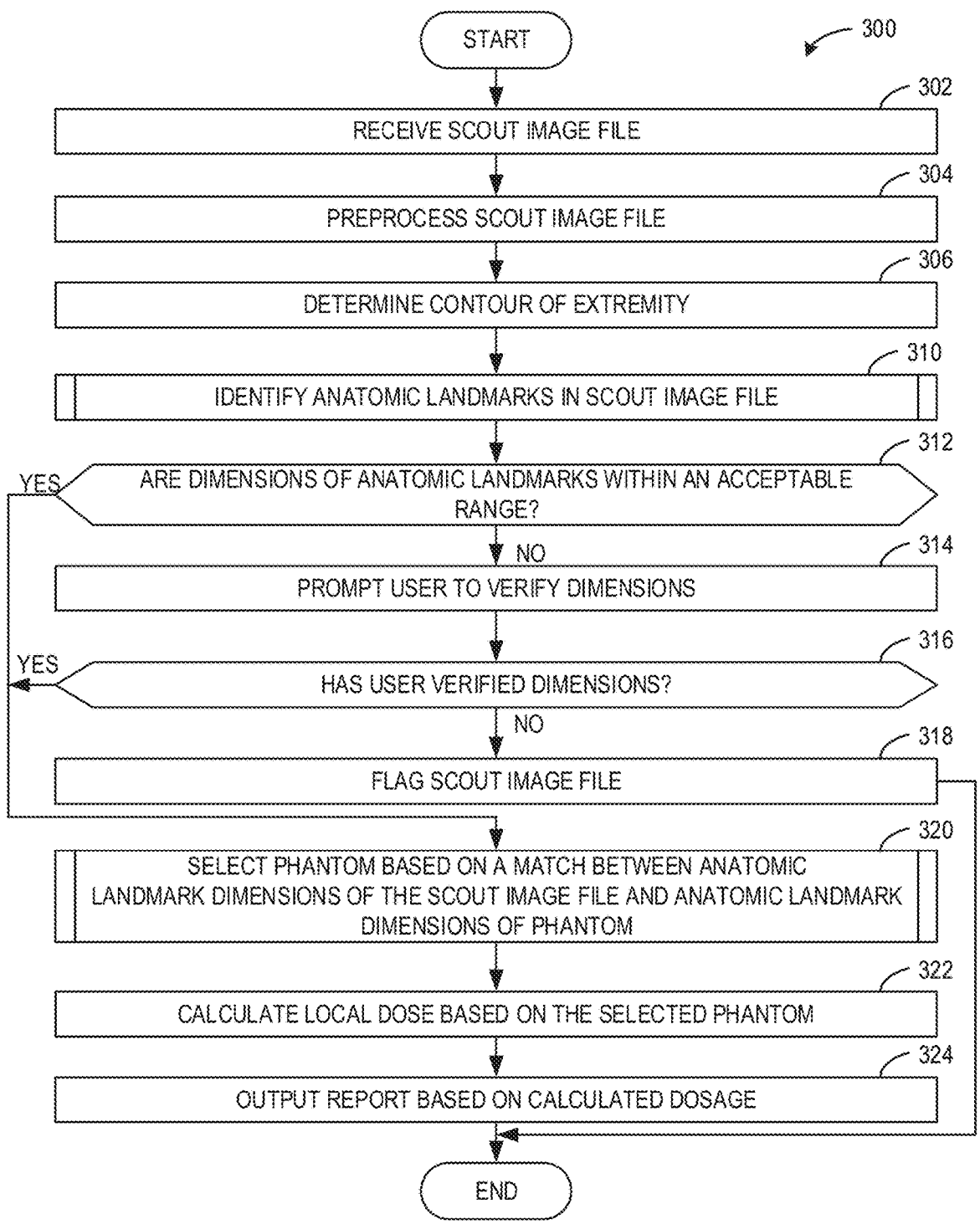
FIGS. 3-6 are flowcharts representative of example machine readable instructions that may be executed to implement the example dose determiner of FIG. 2 to determine radiation doses based on phantom matching.

FIG. 3 is a flowchart 300 representative of example machine readable instructions that can be executed by the dose determiner 112 of FIG. 2 to determine radiation doses based on phantom matching.

At block 302, the receiver 200 receives the scout image file 108 of FIG. 1. At block 304, the scout image processor 204 pre-processes the scout image file 108. For example, the scout image processor 204 may apply one or more filters (e.g., convolution filters) to the scout image file 108 to aid in determining the contour of extremities of the scout image file 108 and in identifying anatomic landmarks in the scout image file 108. At block 306, the scout image processor 204 determines the contour of the extremities (e.g., the edge and/or skin) of the scout image file 108. The contour of the scout image file 108 may be used to determine the dimensions (e.g., diameter) of the scout image file 108 and/or determine correction factors based on the determined dimensions.

At block 310, the dose determiner 112 identifies anatomic landmarks in the scout image file 108, as further described below in conjunction with FIGS. 4 and 5. At block 312, the flag generator 206 determines if the dimensions of the anatomic landmarks are within an acceptable range. For example, if the dose determiner 112 determines that the dimensions of the abdomen is not within an acceptable range (e.g., the dimensions are too large/small), the dimensions may be incorrect and a new scout image file 108 may be needed. If the flag generator 206 determines that the dimensions of the anatomic landmarks are within an acceptable range (block 312: YES), the process continues to block 320, as further described below. If the flag generator 206 determines that the dimensions of the anatomic landmarks are not within an acceptable range (block 312: NO), the flag generator 206 prompts the user to verify the dimensions (block 314). In some examples, the flag generator 206 transmits the prompt to the user via the CT imaging system 100 using the transmitter 202.

At block 316, the flag generator 206 determines if the user (e.g., technician, radiologist, etc.) has verified the dimensions. For example, when the flag generator 206 transmits the prompt, the receiver 200 receives a response from the user/technician verifying or denying the determined dimensions. If the flag generator 206 determines that the user has not verified the dimensions (block 316: NO), the flag generator 206 flags the scout image file 108 (block 318), identifying that there is a problem with the scout file image 108. If the flag generator 206 determines that the user has verified the dimensions (block 316: YES), the method proceeds to block 320. At block 320, the image/phantom comparator 208 selects a phantom (e.g., from the phantom database 114) based on a match between the anatomic landmark dimensions of the scout image file 108 and the anatomic landmark dimensions of the phantom (block 320), as further described below in conjunction with FIG. 6.

At block 322, the dose calculator 210 calculates the local dose based on the selected phantom. As described above in conjunction with FIG. 1, in some embodiments, the dose calculator 210 can calculate the local dose based on the above Equation 2. At block 324, the reporter 212 outputs a report based on the calculated dosage. The report may be output to the technician, the CT imaging system 100, and/or any other person or device.

Figure 4:
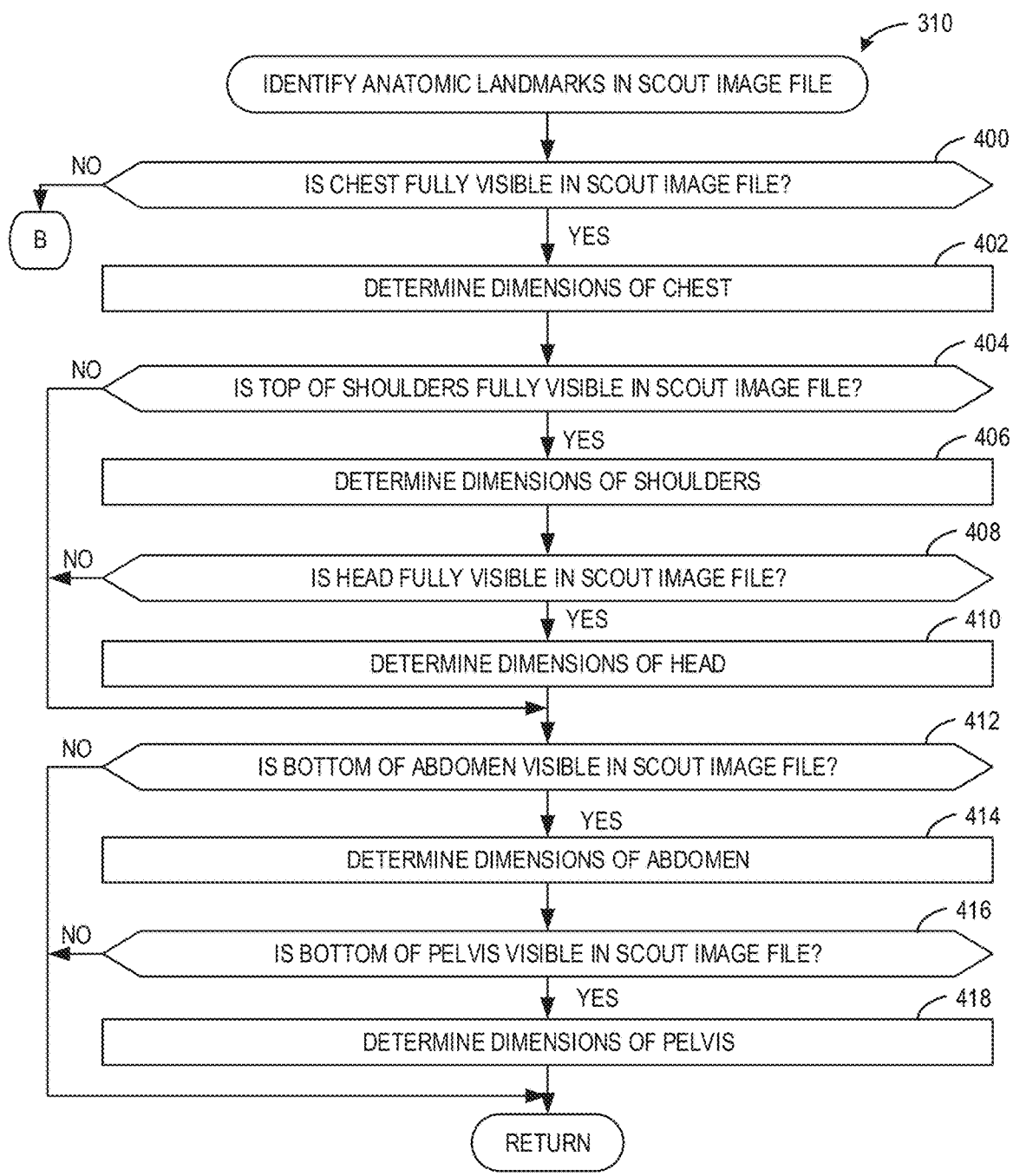
Figure 5:
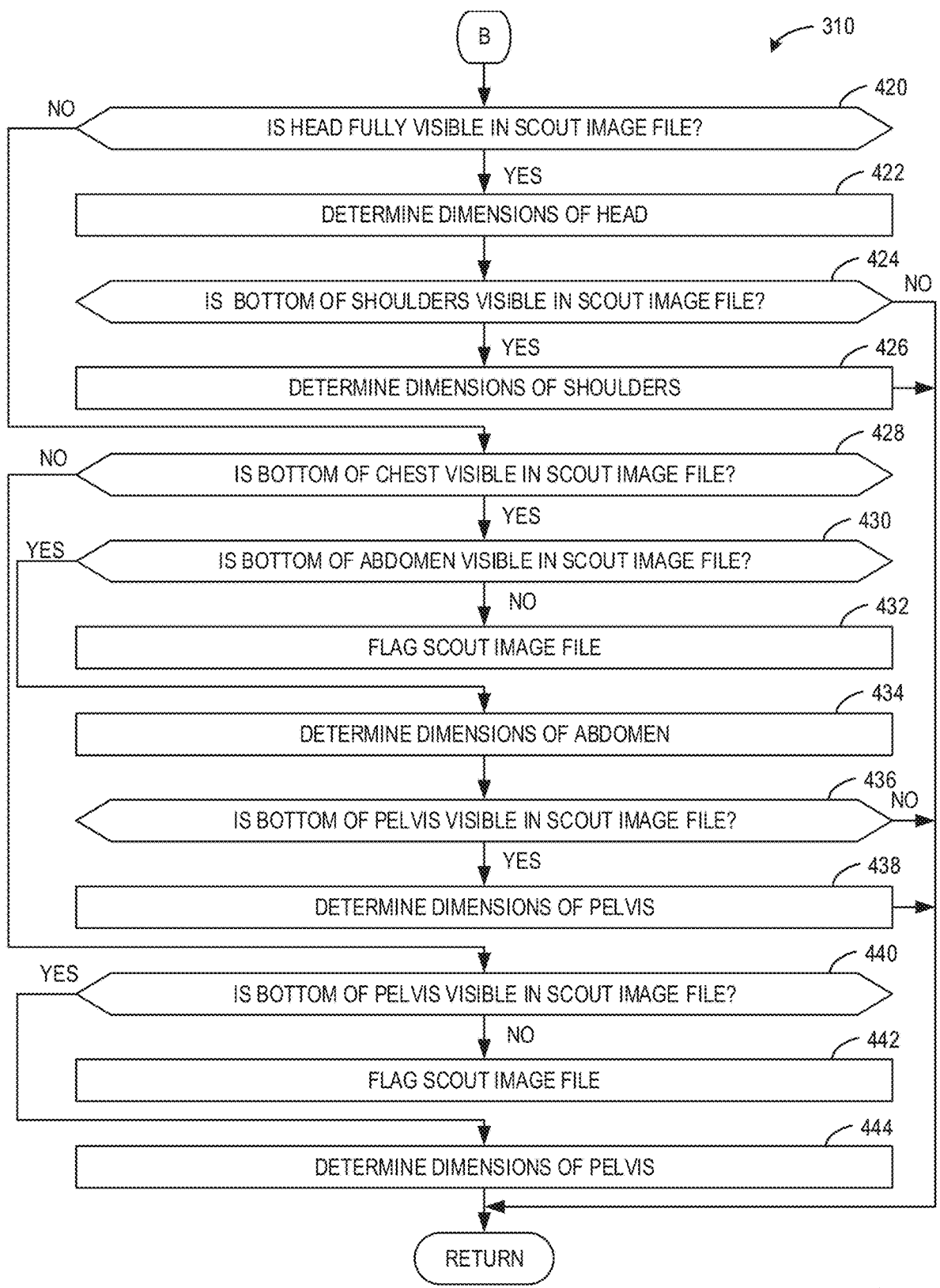

FIGS. 4 and 5 illustrate a flowchart 310 representative of example machine readable instructions that can be executed by the dose determiner 112 of FIG. 2 to identify anatomic landmarks in the scout image file 108, as described above in conjunction with block 310 of FIG. 3. It should be understood that the flowchart 310 shown in FIGS. 4 and 5 is described for illustration not for limitation. Any appropriate landmark determination process can be used. Additionally, some steps can be omitted or added to determine the dimensions of additional or alternative anatomic regions.

At block 400, the scout image processor 204 determines if the chest is fully visible in the scout image file 108. The scout image processor 204 can determine if the chest is fully visible using image processing directed to identifying pixels of greyscale intensity and width associated with a high increase in exposed subject thickness. If the scout image processor 204 determines that the chest is not fully visible in the scout image file 108 (block 400: NO), the process continues to block 420 of FIG. 5, as further described below. If the scout image processor 204 determines that the chest is fully visible in the scout image file 108 (block 400: YES), the scout image processor 204 determines the dimensions of the chest (block 402). For example, the scout image processor 204 can determine the dimensions based on the delineation (e.g., z-axis value) of the top of the chest to the delineation of the bottom of the chest.

At block 404, the scout image processor 204 determines if the top of the shoulder is fully visible in the scout image file 108. If the scout image processor 204 determines that the top of the shoulders is not fully visible in the scout image file 108 (block 404: NO), the process continues to block 412, as further described below. If the scout image processor 204 determines that the top of the shoulders is fully visible in the scout image file 108 (block 404: YES), the scout image processor 204 determines the dimensions of the shoulders (block 406). At block 408, the scout image processor 204 determines if the head is fully visible in the scout image file 108. If the scout image processor 204 determines that the head is not fully visible (block 408: NO), the process continues to block 412. If the scout image processor 204 determines that the head is fully visible (block 410: YES), the scout image processor 204 determines the dimensions of the head (block 410).

At block 412, the scout image processor 204 determines if the bottom of the abdomen (e.g., the bottom of the abdomen delineation) is visible in the scout image file 108. If the scout image processor 204 determines that the bottom of the abdomen is not visible (block 412: NO), the process ends. If the scout image processor 204 determines that the bottom of the abdomen is visible (block 412: YES), the scout image processor 204 determines the dimensions of the abdomen (block 414). At block 416, the scout image processor 204 determines if the bottom of the pelvis is visible in the scout image file 108. If the scout image processor 204 determines that the bottom of the pelvis is not visible in the scout image file 108 (block 416: NO), the process ends. If the scout image processor 204 determines that the bottom of the pelvis is visible in the scout image file 108 (block 416: YES), the scout image processor 204 determines the dimensions of the pelvis (block 418).

At block 420 of FIG. 5, the scout image processor 204 determines if the head is fully visible in the scout image file 108. If the scout image processor 204 determines that the head is not fully visible in the scout image file 108 (block 420: NO), the process continues to block 428, as further described below. If the scout image processor 204 determines that the head is fully visible in the scout image file 108 (block 420: YES), the scout image processor 204 determines the dimensions of the head (block 422). At block 424, the scout image processor 204 determines if the bottom of the shoulders is visible in the scout image file 108. If the scout image processor 204 determines that the bottom of the shoulders is visible in the scout image file 108 (block 424: YES), the scout image processor 204 determines the dimensions of the shoulders (block 426), and the process ends. If the scout image processor 204 determines that the bottom of the shoulders is not visible in the scout image file 108 (block 424: NO), the process ends.

At block 428, the scout image processor 204 determines if the bottom of the chest is visible in the scout image file 108. If the scout image processor 204 determines that the bottom of the chest is not visible in the scout image file 108 (block 428: NO), the process continues to block 440, as further described below. If the scout image processor 204 determines that the bottom of the chest is visible in the scout image file 108 (block 428: YES), the scout image processor 204 determines if the bottom of the abdomen is visible in the scout image file 108 (block 430). If the scout image processor 204 determines that the bottom of the abdomen is not visible in the image (block 430: NO), the flag generator 206 flags the scout image (block 432) because none of the dimensions of the anatomic landmarks can be determined. If the scout image processor 204 determines that the bottom of the abdomen is visible in the image (block 430: YES), the scout image processor 204 determines the dimensions of the abdomen (block 434). At block 436, the scout image processor 204 determines if the bottom of the pelvis is visible in the scout image file 108. If the scout image processor 204 determines that the bottom of the pelvis is not visible (block 436: NO), the process ends. If the scout image processor 204 determines that the bottom of the pelvis is visible (block 436: YES), the scout image processor 204 determines the dimensions of the pelvis (block 438).

At block 440, the scout image processor 204 determines if the bottom of the pelvis is visible in the scout image file 108. If the scout image processor 204 determines that the bottom of the pelvis is not visible in the scout image file 108 (block 440: NO), the example flag generator 206 flags the scout image file 108 (block 442). If the scout image processor 204 determines that the bottom of the pelvis is visible in the scout image file 108 (block 440: YES), the scout image processor 204 determines the dimensions of the pelvis (block 444).

Figure 6:
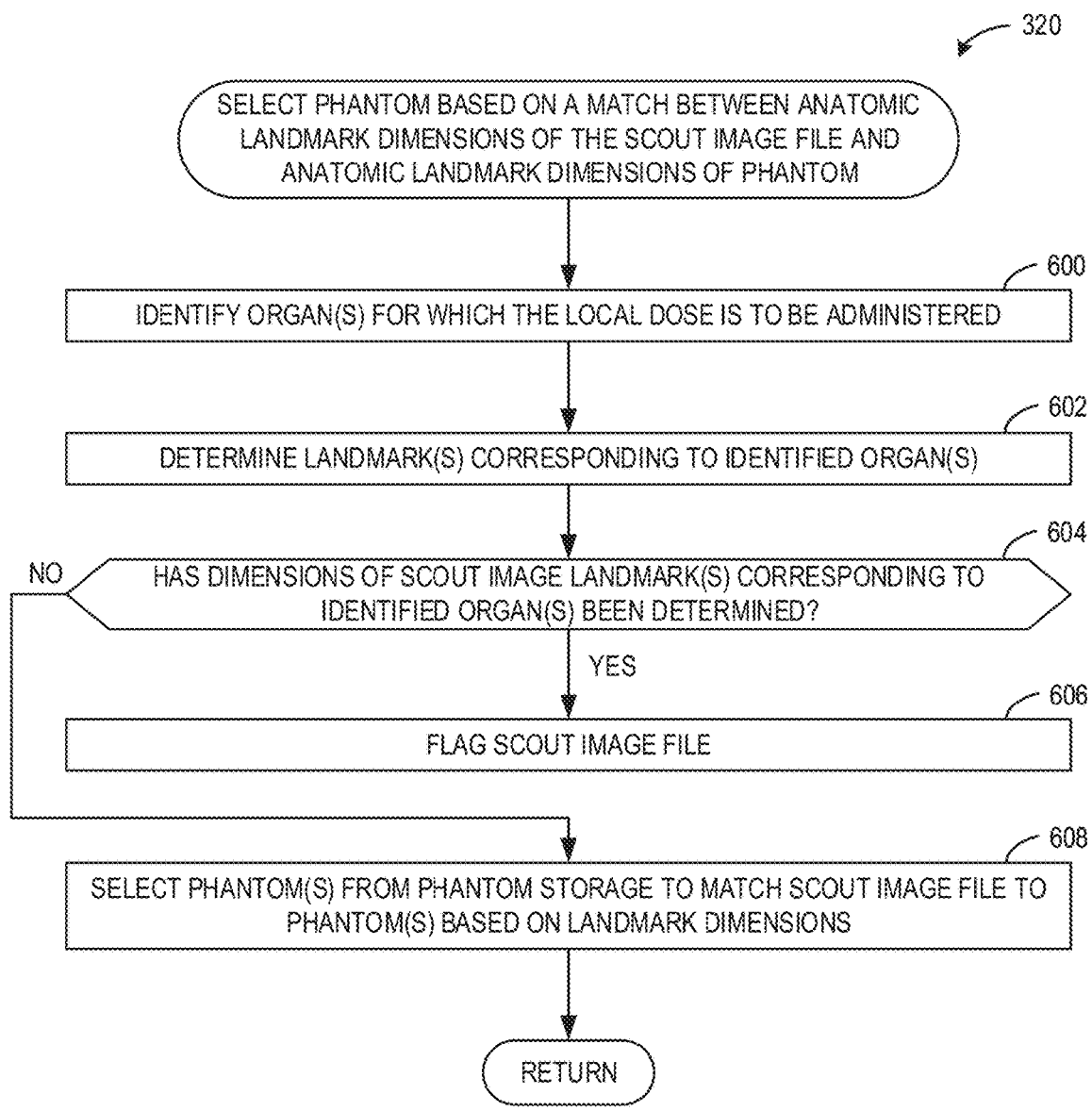

FIG. 6 is a flowchart 320 representative of example machine readable instructions that can be executed by the dose determiner 112 of FIG. 2 to select a phantom based on a match between anatomic landmark dimensions of the scout image file and anatomic landmark dimensions of the phantom, as described above in conjunction with block 320 of FIG. 3.

At block 600, the image/phantom comparator 208 identifies organ(s) for which the local dose is to be administered. In some examples, the scout image file 108 may include data that corresponds to an organ(s) for which the local dose is to be calculated (e.g., the organ being selected by a technician to be included in the scout image file 108). In some examples, the organ(s) to which the local dose is to be calculated is based on the anatomic landmarks that have been identified in the scout image file 108. For example, if the scout image file 108 only includes a chest, the image/phantom comparator 208 deduces irradiated regions of the chest based on the locations of the beginning and the end of the scout image 108 and the determined anatomic regions. In such an example, the image/phantom comparator 208 determines the organs within the irradiated regions (e.g., the chest) to correspond to the local dose based on the irradiated regions. In some examples, the scout image file 108 may include a clinical indication to know what region should have been irradiated. For example, a prescribed chest exam will identify chest organs for irradiation. The approach for identifying organs corresponding to the local dose may be based on user and/or manufacture preferences.

At block 602, the image/phantom comparator 208 determines the anatomic landmark(s) corresponding to the identified organ(s). For example, when the technician selects an organ(s), and the organ(s) is identified in the scout image file 108. In such an example, the image/phantom comparator 208 determines which anatomic landmark(s) correspond to the identified organ(s). At block 604, the image/phantom comparator 208 determines if the dimensions of the scout image landmark(s) corresponding to the identified organ(s) have been determined. For example, if the identified organ is a heart, then the image/phantom comparator 208 determines that the chest is the anatomic landmark. In such an example, the image/phantom comparator 208 determines if the dimensions of the chest have been determined (e.g., are fully visible) in the scout image file 108.

If the image/phantom comparator 208 determines that the dimensions of the scout image anatomic landmark corresponding to the identified organ(s) have not been determined (block 604: NO), the flag generator 206 flags the scout image file 108 (block 606). The flag generator 206 flags the scout image file 108 because the scout image file 108 does not include a full/clear image of the anatomic landmark corresponding to the identified organ. If the image/phantom comparator 208 determines that the dimensions of the scout image anatomic landmark corresponding to the identified organ(s) have been determined (block 604: YES), the image/phantom comparator 208 selects one or more phantom(s) from the phantom database 114 to match the scout image file 108 to one or more phantom(s) based on the landmark dimensions (block 608). In some examples, the image/phantom comparator 208 transmits instructions including the dimensions of the anatomic landmarks of interest (e.g., via the transmitter 202) to the phantom database 114. In response to receiving the instructions, the phantom database 114 responds with one or more phantoms that match the dimensions of the anatomic landmarks of interest. In some examples, the image/phantom comparator 208 is able to interface with the phantom database 114 directly to query the phantom database 114 to select a phantom that matches the dimensions of the anatomic landmark(s) of interest of the scout image file 108.

Figure 7:
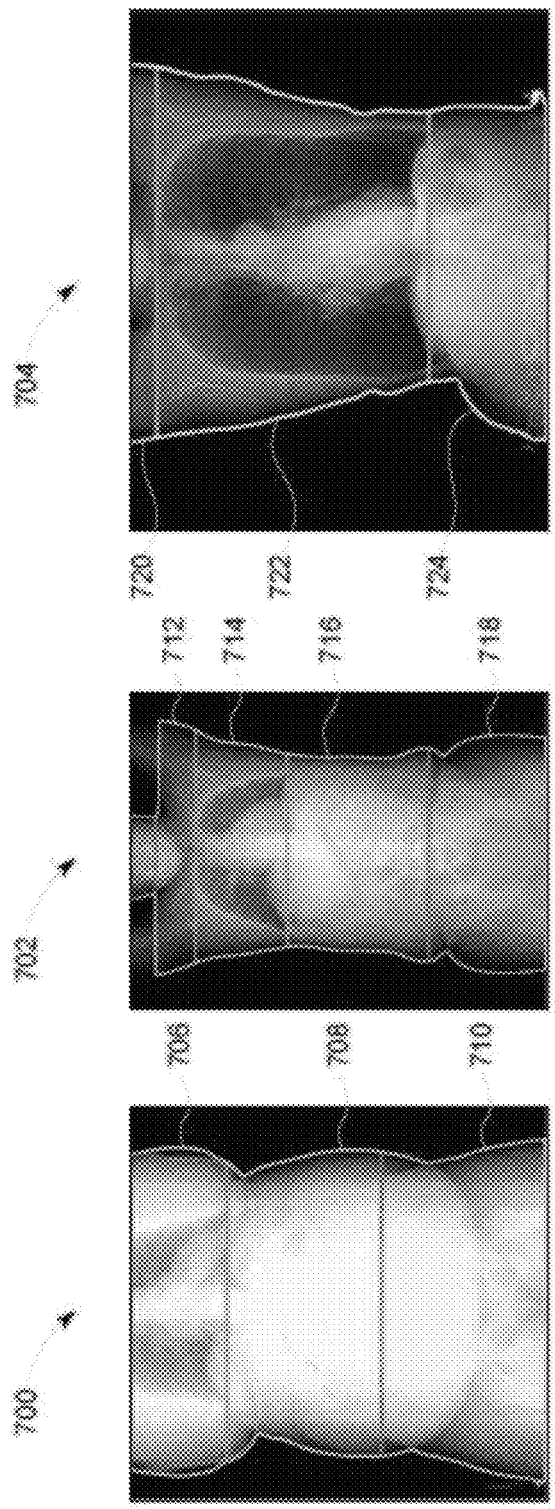
FIG. 7 illustrates example scout images that have been processed by the dose determiner of FIG. 2 to identify anatomical landmarks to be matched with phantoms.

FIG. 7 illustrates example scout images 700, 702, 704 that may be include in one or more scout image files 108 of FIG. 1. The scout image 700 shows a chest 706, an abdomen 708, and a pelvis 710. The scout image 702 shows shoulders 712, a chest 714, an abdomen 716, and a pelvis 718. The scout image 704 shows shoulders 720, a chest 722, and an abdomen 724.

The scout image 700 is an image of an exposed subject generated by the CT imaging system 100 of FIG. 1. The dose determiner 112 receives the scout image and determines the dimensions of anatomic landmarks that are fully included in the scout image 700 by determining the contour of the scout image 700 (e.g., the outer regions) and delineating the anatomic landmarks. In the scout image 700, the abdomen 708 is fully visible and the chest 706 and pelvis 710 are not fully visible. Accordingly, the dose determiner 112 may determine the dimensions of the abdomen 708 and may calculate local doses for one or more organs within the abdomen 708.

The scout image 702 is another image of an exposed subject generated by the CT imaging system 100 of FIG. 1. In the scout image 702, the shoulders 712, the chest 714, and the abdomen 716 are fully visible and the pelvis 718 is partially visible. Accordingly, the dose determiner 112 may determine the dimensions of the shoulders 712, the chest 714, and the abdomen 716 and may calculate local doses for one or more organs within the chest 714 and abdomen 716.

The scout image 704 is another image of an exposed subject generated by the CT imaging system 100 of FIG. 1. In the scout image 704, the chest 722 is fully visible and the shoulders 720 and the abdomen 724 are partially visible. Accordingly, the dose determiner 112 may determine the dimensions of the chest 714 and may calculate local doses for one or more organs within the chest 714.

Figure 8:
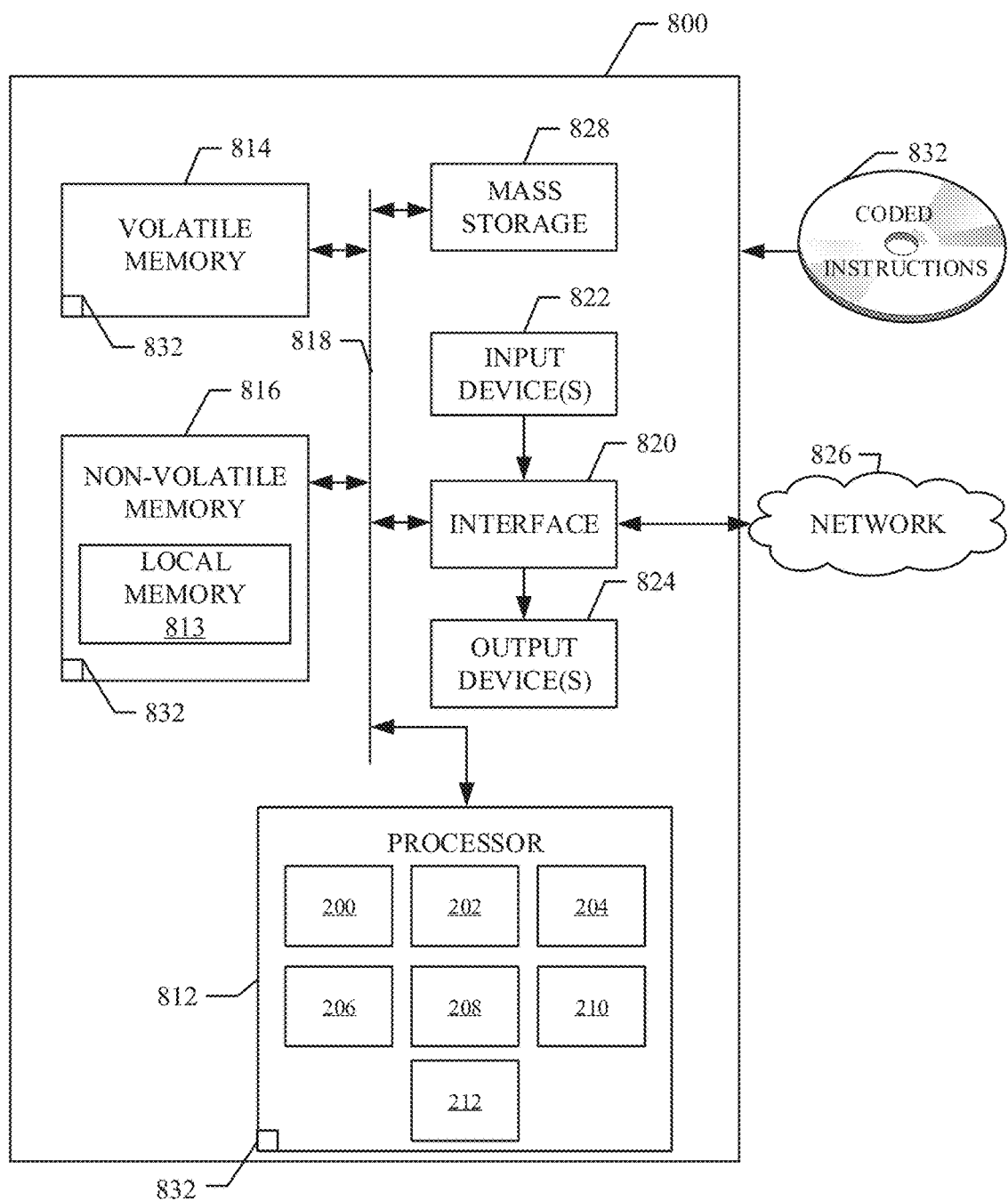
FIG. 8 is a block diagram of a processing system structured to execute the example machine readable instructions of FIGS. 3-6 to implement the example dose determiner of FIG. 2.

FIG. 8 is a block diagram of an example processor platform 800 structured to executing the instructions of FIG. 8 to implement the dose determiner 112 of FIG. 1 and/or 2. The processor platform 800 can be, for example, a server, a personal computer, a mobile device (e.g., a cell phone, a smart phone, a tablet such as an iPad™), a personal digital assistant (PDA), an Internet appliance, or any other type of computing device.

The processor platform 800 of the illustrated example includes a processor 812. The processor 812 of the illustrated example is hardware. For example, the processor 812 can be implemented by integrated circuits, logic circuits, microprocessors or controllers from any desired family or manufacturer.

In the examples, the machine readable instructions include a program for execution by one or more processors such as the processor 812 shown in the example processor platform 800 discussed below in connection with FIG. 8. The machine readable instructions may be stored on a tangible computer readable storage medium such as a CD-ROM, a floppy disk, a hard drive, a digital versatile disk (DVD), a Blu-ray disk, or a memory associated with the processor 812, but the entire program and/or parts thereof could alternatively be executed by a device other than the processor 812 and/or embodied in firmware or dedicated hardware.

The processor 812 of the illustrated example includes a local memory 813 (e.g., a cache). The example processor 812 of FIG. 8 executes the instructions of FIGS. 3-6 to implement the receiver 200, the transmitter 202, the scout imager processor 204, the flag generator 206, the image/phantom comparator 208, the dose calculator 210, and/or the reporter 212.

The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a clock controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

The coded instructions 832 of FIG. 3-6 may be stored in the mass storage device 828, in the volatile memory 814, in the non-volatile memory 816, and/or on a removable tangible computer readable storage medium such as a CD or DVD.

From the foregoing, it will be appreciated that the above disclosed methods, apparatus, and articles of manufacture have been disclosed for determining radiation doses based on phantom matching. In the field of CT scanning, conventional techniques of measuring the weight, age, and/or gender of a patient prior to completing the scan was done to precisely calculate the dose of radiation to be administered to the patient. However, a match based on weight, age, and/or gender may not be accurate for people of the same weight, age, and/or gender but different dimensions, thereby leading to inaccurate doses. For example, a scout may match a phantom model based on weight, age, and/or gender, however the dimensions of the scout may include a large chest and a small abdomen and the phantom model may include a small chest and a large abdomen, thereby corresponding to different appropriate radiation doses.

Examples disclosed herein include processing scout images to identify anatomical landmarks (e.g., head, chest, abdomen, etc.) based on the image. For example, disclosed examples may include determining (A) what landmarks are included in the scout image and (B) the dimensions of the determined landmarks. The disclosed examples further include matching the landmarks with landmarks of the phantom models as opposed to matching based on weight, age, and/or gender. Examples disclosed herein increase the accuracy of radiation dose administered to the patient, helping to ensure that high quality CT images are acquired at the least possible dose of radiation.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
   means for processing a first scout image to determine a first set of dimensions of a first anatomical landmark of a first scout image file;
   means for flagging the first scout image when at least one of (A) the first anatomical landmark in the first scout image does not include an organ (B) the first set of dimensions of the first anatomic landmark cannot be determined, or (C) the first set of dimensions are outside of a predefined range, the flag to prompt a capture of a second scout image;
   the means for processing to process the second scout image to determine a second set of dimensions of a second anatomical landmark of a second scout image file;
   means for selecting a phantom model based on the second set of dimensions, the phantom model including the second anatomical landmark with a third set of dimensions that match the second set of dimensions; and means for calculating a radiation dose for an organ in the second anatomical landmark based on the selected phantom.

2. The apparatus of claim 1, wherein the processing means is to (A) determine a contour of the first scout image and (B) delineate the first scout image to determine the first set of dimensions.

3. The apparatus of claim 1, wherein the organ in the second anatomical landmark is identified by a user.

4. The apparatus of claim 1, wherein the calculating means is to calculate the radiation dose based on at least one of a number of organ pixels of the phantom model, a computed tomography (CT) dose index, correction factors corresponding to a size of an imaged subject, or a fixed dose spread function.

5. The apparatus of claim 1, further including means for outputting a report based on the calculated radiation dose.

6. The apparatus of claim 1, wherein the match corresponds to a difference between the second set of dimensions and the third set of dimensions being within a predefined threshold.

7. The apparatus of claim 1, wherein the match corresponds to a first difference between the second set of dimensions and the third set of dimensions being less than a second difference between the second set of dimensions and any other sets of dimensions for any other phantom in a database.

8. An apparatus comprising:
an image processor configured to process a first scout image to determine a first set of dimensions of a first anatomical landmark of a first scout image file;
a flag generator configured to flag the first scout image when at least one of (A) the first anatomical landmark in the first scout image does not include an organ (B) the image processor cannot determine the first set of dimensions of the first anatomic landmark, or (C) the first set of dimensions are outside of a predefined range, the flag to prompt a capture of a second scout image; and
a dose calculator configured to calculate a radiation dose for an organ in a second anatomical landmark of a second scout image file taken in response to the flag.

9. The apparatus of claim 8, wherein the image processor is configured to (A) determine a contour of the first scout image and (B) delineate the first scout image to determine the first set of dimensions.

10. The apparatus of claim 8, wherein the organ in the second anatomical landmark is identified by a user.

11. The apparatus of claim 8, wherein the dose calculator is to calculate the radiation dose based on at least one of a number of organ pixels of a phantom model that corresponds to the second scout image file, a computed tomography (CT) dose index, correction factors corresponding to a size of an imaged subject, or a fixed dose spread function.

12. The apparatus of claim 8, further including a reporter configured to output a report based on the calculated radiation dose.

13. The apparatus of claim 8, further including a transmitter to transmit the flag to an imaging device to prompt the capture of the second scout image file.

14. A tangible computer readable storage medium comprising instructions which, when executed, cause a machine to at least:
process a first scout image to determine a first set of dimensions of a first anatomical landmark of a first scout image file;
flag the first scout image when at least one of (A) the first anatomical landmark in the first scout image does not include an organ (B) the first set of dimensions of the first anatomic landmark cannot be determined, or (C) the first set of dimensions are outside of a predefined range, the flag to prompt a capture of a second scout image; and
calculate a radiation dose for an organ in a second anatomical landmark of a second scout image file taken in response to the flag.

15. The tangible computer readable storage medium of claim 14, wherein the instructions cause the machine to (A) determine a contour of the first scout image and (B) delineate the first scout image to determine the first set of dimensions.

16. The tangible computer readable storage medium of claim 14, wherein the instructions cause the machine to calculate the radiation dose based on at least one of a number of organ pixels of a phantom model that corresponds to the second scout image file, a computed tomography (CT) dose index, correction factors corresponding to a size of an imaged subject, or a fixed dose spread function.

17. The tangible computer readable storage medium of claim 14, wherein the instructions cause the machine to output a report based on the calculated radiation dose.

18. The tangible computer readable storage medium of claim 14, wherein the instructions cause the machine to select a phantom model that corresponds to the second scout image file, the calculation of the radiation dose for the organ being based on the selected phantom.

19. The tangible computer readable storage medium of claim 18, wherein the instructions cause the machine to select the phantom model by:
identifying the organ;
determining the second anatomical landmark corresponding to the identified organ; and
selecting the phantom model including a third set of dimensions that match a second set of dimensions of the second anatomical landmark of the second scout image file.

20. The tangible computer readable storage medium of claim 14, wherein the instruction cause the machine to transmit the flag to an imaging device to prompt the capture of the second scout image file.

* * * * *